United States Patent
Suyama

(10) Patent No.: US 10,514,535 B2
(45) Date of Patent: Dec. 24, 2019

(54) IMAGE PICKUP UNIT, CAPSULE ENDOSCOPE, AND MANUFACTURING METHOD OF CAPSULE ENDOSCOPE

(71) Applicant: OLYMPUS CORPORATION, Tokyo (JP)

(72) Inventor: Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 297 days.

(21) Appl. No.: 15/402,583

(22) Filed: Jan. 10, 2017

(65) Prior Publication Data
US 2017/0123200 A1    May 4, 2017

Related U.S. Application Data

(63) Continuation of application No. PCT/JP2015/063308, filed on May 8, 2015.

(30) Foreign Application Priority Data

Jul. 16, 2014    (JP) .................................. 2014-146197

(51) Int. Cl.
*G02B 23/24*     (2006.01)
*A61B 1/04*      (2006.01)
(Continued)

(52) U.S. Cl.
CPC ...... *G02B 23/2484* (2013.01); *A61B 1/00124* (2013.01); *A61B 1/041* (2013.01); *H04N 5/2256* (2013.01); *H04N 2005/2255* (2013.01)

(58) Field of Classification Search
CPC ........ H05K 1/144; H05K 1/148; H05K 1/145; H05K 1/147; G02B 23/2484;
(Continued)

(56) References Cited

U.S. PATENT DOCUMENTS

2003/0030143 A1*  2/2003  Wennemuth ........ H01L 23/3114
                                                              257/738
2005/0014395 A1*  1/2005  Fjelstad ................. H05K 1/147
                                                                439/61
(Continued)

FOREIGN PATENT DOCUMENTS

EP    2002780 A1   12/2008
EP    2130480 A1   12/2009
(Continued)

OTHER PUBLICATIONS

International Search Report dated Aug. 4, 2015 issued in PCT/JP2015/063308.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An image pickup unit of an embodiment includes: a first substrate on which an image pickup device is mounted; a first intermediate wiring board including a first wire, one end of the first wire electrically connected to the first substrate, the other end of the first wire including a first electrode pad; a second substrate on which an electronic component is mounted; and a second intermediate wiring board including a second wire, one end of the second wire electrically connected to the second substrate, and the other end of the second wire including a second electrode pad, wherein the first electrode pad and the second electrode pad coming into close contact and fixed in an electrically connected state are bent and deformed.

6 Claims, 7 Drawing Sheets

(51) Int. Cl.
   *A61B 1/00*   (2006.01)
   *H04N 5/225*   (2006.01)
(58) Field of Classification Search
   CPC .............. A61B 1/0011; A61B 1/00112; A61B 1/00124; A61B 1/041; A61B 1/051; H04N 2005/2255
   USPC ..................................................... 29/890.125
   See application file for complete search history.

(56) References Cited

U.S. PATENT DOCUMENTS

| | | | |
|---|---|---|---|
| 2006/0264704 A1* | 11/2006 | Fujimori | A61B 1/04 600/101 |
| 2008/0312504 A1* | 12/2008 | Kimoto | A61B 1/00016 600/118 |
| 2008/0315402 A1* | 12/2008 | Hwang | H05K 1/0203 257/712 |
| 2010/0016667 A1 | 1/2010 | Segawa et al. | |
| 2011/0269319 A1* | 11/2011 | Cheng | H01R 12/7082 439/67 |
| 2016/0141219 A1* | 5/2016 | Liu | G01L 19/14 257/737 |

FOREIGN PATENT DOCUMENTS

| | | |
|---|---|---|
| JP | H07-226569 A | 8/1995 |
| JP | 2003-219284 A | 7/2003 |
| JP | 2004-014235 A | 1/2004 |
| JP | 2004-179830 A | 6/2004 |
| JP | 2008-246148 A | 10/2008 |
| JP | 2008-307187 A | 12/2008 |
| JP | 2010-187304 A | 8/2010 |
| JP | 2013-048826 A | 3/2013 |
| WO | WO 2008/123464 A1 | 10/2008 |

* cited by examiner

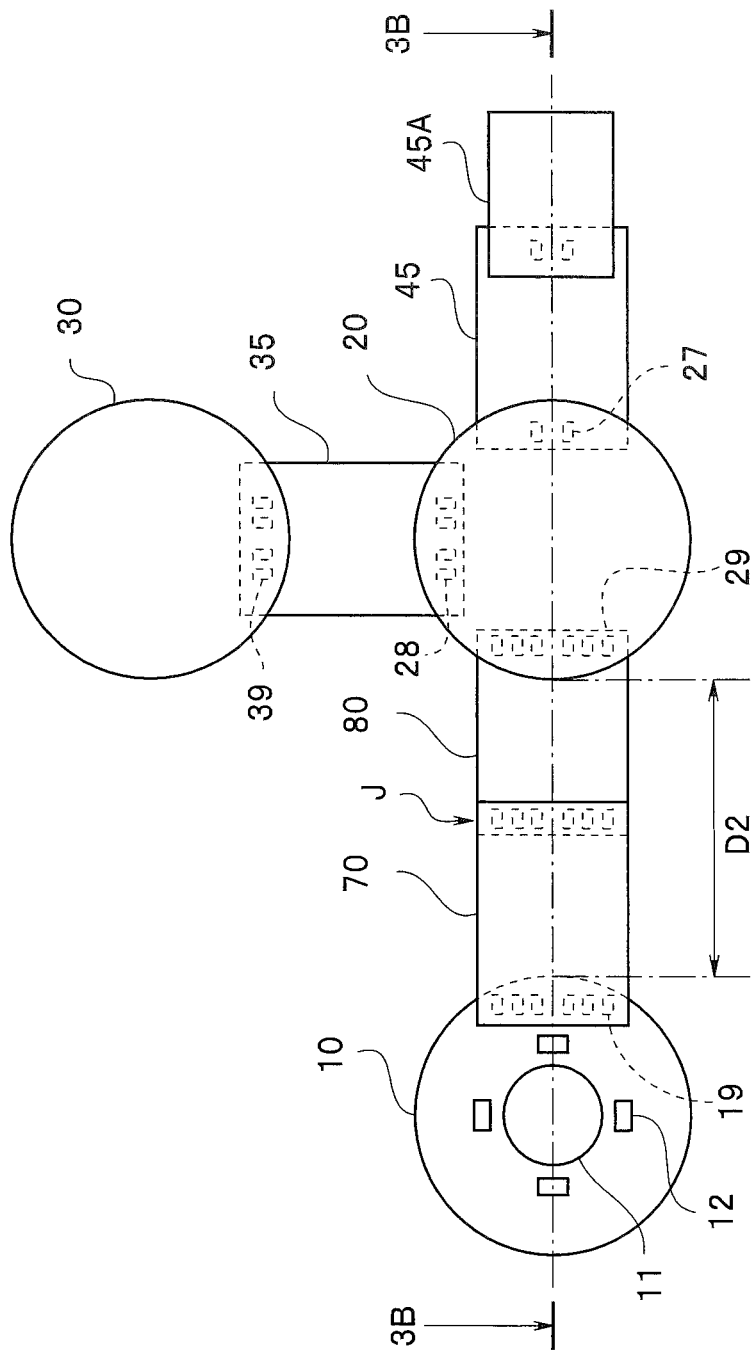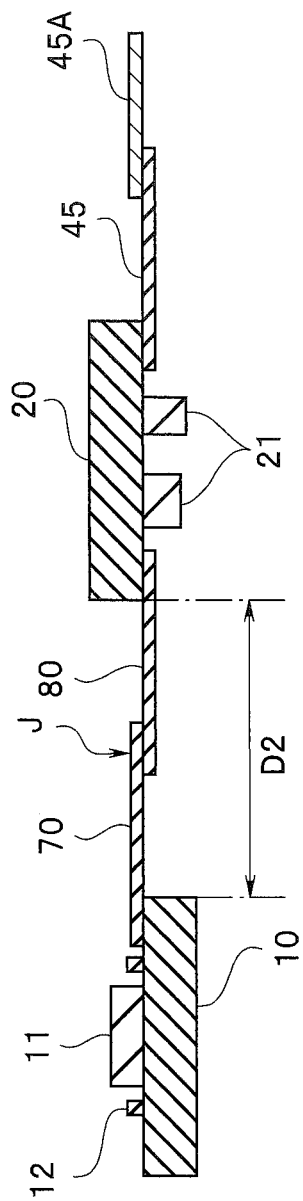
FIG. 3A
FIG. 3B

IMAGE PICKUP UNIT, CAPSULE ENDOSCOPE, AND MANUFACTURING METHOD OF CAPSULE ENDOSCOPE

CROSS REFERENCE TO RELATED APPLICATION

This application is a continuation application of PCT/JP2015/063308 filed on May 8, 2015 and claims benefit of Japanese Application No. 2014-146197 filed in Japan on Jul. 16, 2014, the entire contents of which are incorporated herein by this reference.

BACKGROUND OF THE INVENTION

1. Field of the Invention

The present invention relates to an image pickup unit electrically connecting a first substrate, on which an image pickup device is mounted, and a second substrate, on which an electronic component is mounted, through a first intermediate wiring board and a second intermediate wiring board, a capsule endoscope including the image pickup unit, and a manufacturing method of the capsule endoscope.

2. Description of the Related Art

A capsule endoscope having an image pickup function and a wireless transmission function is coming into widespread use. The capsule endoscope is swallowed by an examinee, and the capsule endoscope moves inside of digestive tracts, such as stomach and small intestine, along with peristaltic motion, until the capsule endoscope is naturally discharged. The capsule endoscope uses the image pickup function to pick up images inside of an organ.

The images picked up by the capsule endoscope while the capsule endoscope moves inside of the digestive tracts are transmitted as image signals by a wireless transmission function, to an external apparatus provided outside of a subject. The images are stored in a memory of the external apparatus. The examinee can carry the external apparatus having a wireless reception function and a memory function to freely act after swallowing the capsule endoscope. After observation by the capsule endoscope, the images stored in the memory of the external apparatus are displayed on a display or the like to perform diagnosis or the like. Here, miniaturization of the capsule endoscope (shortening and reduction in diameter) is an important issue in order to minimize invasion.

Japanese Patent Application Laid-Open Publication No. 2013-48826 discloses a capsule endoscope housing an image pickup unit in a housing, the image pickup unit including a wiring board in which a plurality of substantially circular substrate portions are linked through flexible substrate portions.

Japanese Patent Application Laid-Open Publication No. 2004-14235 discloses a connection member capable of fixing a conductor and a conductor after the conductor and the conductor are temporarily fixed in a closely contact and electrically connected state. In an image pickup unit using the connection member, action is checked in the temporarily fixed state, and a wiring board can be used by replacing only a substrate portion with an abnormality. Therefore, productivity is excellent.

SUMMARY OF THE INVENTION

An image pickup unit of an embodiment of the present invention includes: a first substrate on which an image pickup device is mounted; a first intermediate wiring board including a first wire, one end of the first wire being electrically connected to the first substrate, another end of the first wire including a first electrode pad; a second substrate on which an electronic component is mounted; and a second intermediate wiring board including a second wire, one end of the second wire being electrically connected to the second substrate, another end of the second wire including a second electrode pad, wherein the first electrode pad and the second electrode pad coming into close contact and fixed in an electrically connected state are bent and deformed.

A capsule endoscope of another embodiment includes: a first substrate on which an image pickup device is mounted, the first substrate including an external electrode electrically connected to the image pickup device; a flexible first intermediate wiring board including a first wire, one end of the first wire being electrically connected to the external electrode, another end of the first wire including a first electrode pad; a second substrate on which an electronic component is mounted, the second substrate including a connection electrode electrically connected to the electronic component; a flexible second intermediate wiring board including a second wire, one end of the second wire being electrically connected to the connection electrode, another end of the second wire including a second electrode pad coming into close contact with the first electrode pad and fixed in an electrically connected state; and a housing in which the first substrate, the second substrate, the first intermediate wiring board, and the second intermediate wiring board are housed, the housing being a capsule in a rotationally symmetric shape with a center axis in a longitudinal direction serving as an axis of rotational symmetry, wherein a main surface of the first substrate and a main surface of the second substrate are arranged in parallel, and the first electrode pad and the second electrode pad are bent and deformed and are inserted between the first substrate and the second substrate.

Another embodiment provides a manufacturing method of a capsule endoscope, in which an image pickup unit including a first substrate, a second substrate, a first intermediate wiring board, and a second intermediate wiring board is housed in a housing, and the first substrate and the second substrate are electrically connected through the first intermediate wiring board and the second intermediate wiring board, the manufacturing method including: mounting an image pickup device on the first substrate including an external electrode to electrically connect the image pickup device and the external electrode; mounting an electronic component on the second substrate including a connection electrode to electrically connect the electronic component and the connection electrode; manufacturing the first intermediate wiring board including a first wire, one end of the first wire being electrically connected to the external electrode, another end of the first wire including a first electrode pad, and manufacturing the second intermediate wiring board including a second wire, one end of the second wire being electrically connected to the connection electrode, another end of the second wire including a second electrode pad; temporarily fixing the first electrode pad and the second electrode pad by a sticky layer pattern around the first electrode pad, in a state that the first electrode pad and the second electrode pad are in close contact and electrically connected; supplying drive power to the image pickup device through the second substrate to check action; curing an adhesive layer around the first electrode pad to fix the first electrode pad and the second electrode pad; arranging a main surface of the first substrate and a main surface of the second substrate parallel to each other; bending and deforming the fixed first electrode pad and the second electrode pad to insert the fixed first electrode pad and the first electrode pad between the first substrate and the second substrate; and housing the image pickup unit including the first substrate, the second substrate, the first intermediate wiring board, and the second intermediate wiring board in the housing.

BRIEF DESCRIPTION OF THE DRAWINGS

FIG. 3A is a plan view of an image pickup unit of the first embodiment;

FIG. 3B is a cross-sectional view of the image pickup unit of the first embodiment, along a line IIIB-IIIB of FIG. 3A;

DETAILED DESCRIPTION OF THE PREFERRED EMBODIMENT(S)

<First Embodiment>

Figure 1:
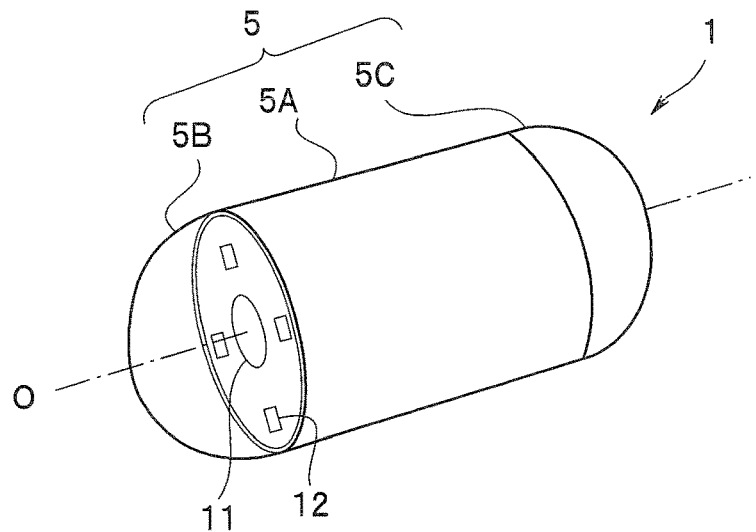
FIG. 1 is a perspective view of a capsule endoscope of a first embodiment.
Figure 2:
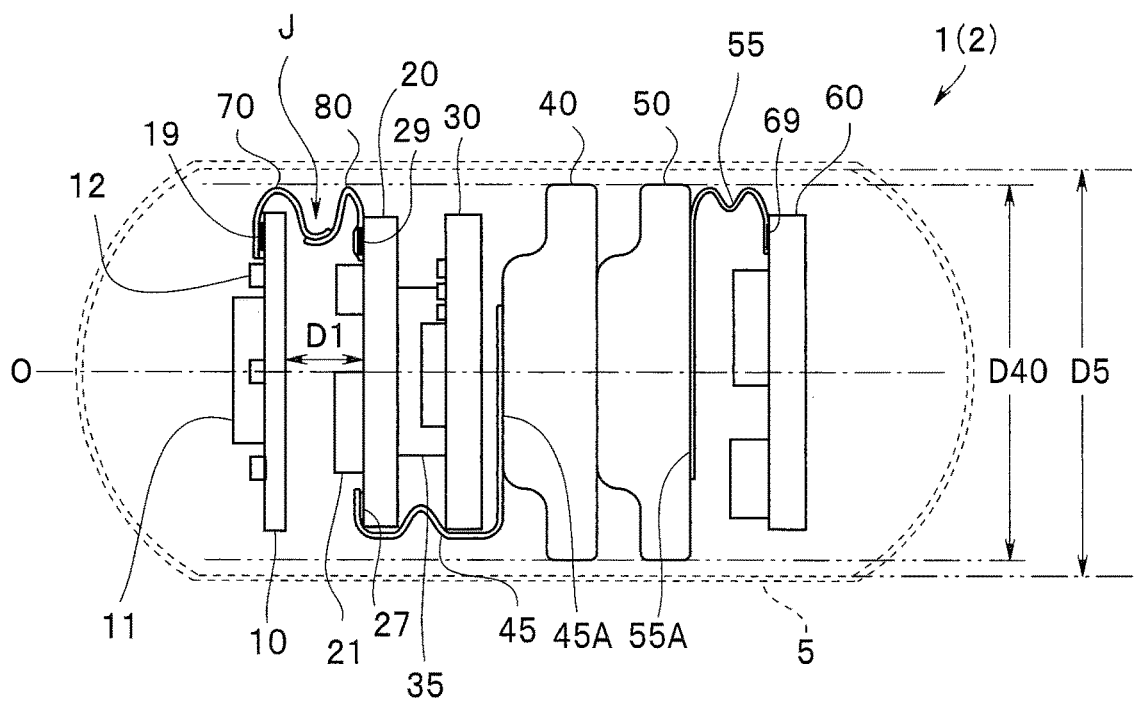
FIG. 2 is a cross-sectional view of the capsule endoscope of the first embodiment.

As shown in FIGS. 1 and 2, an image pickup unit 2 is housed in a capsule housing 5 in a capsule endoscope (hereinafter, called "endoscope") 1 of the present embodiment. Note that FIGS. 3A and 3B are a plan view and a cross-sectional view of part of the image pickup unit 2 before the image pickup unit 2 is housed in the housing 5.

Note that in the following description, drawings based on embodiments are schematic drawings, and a relationship between thickness and width of each part, a ratio of the thickness of respective parts, and the like are different from the reality. The relationship or the ratio of dimensions between the drawings may also be different in some parts of the drawings. Furthermore, illustration of part of constituent elements may be omitted.

The housing 5 includes: a cylindrical main body portion 5A; and substantially hemispheric end portion cover portions 5B and 5C at both ends of the main body portion 5A. The end portion cover portion 5B is made of a transparent material, and the main body portion 5A and the end portion cover portion 5C are made of an integrated non-transparent material.

The elongated housing 5 has a rotationally symmetric shape, in which a center axis O in a longitudinal direction is an axis of rotational symmetry. A length L of the housing 5, that is, a length in a direction of the center axis O is 25 mm to 35 mm, and a diameter D5 in an orthogonal direction of the center axis O is 5 mm to 15 mm, for example.

As shown in FIGS. 2 and 3A, the image pickup unit 2 housed inside of the housing 5 includes a first substrate 10, a second substrate 20, a third substrate 30, batteries 40 and 50, and a fourth substrate 60, all of which are substantially circular in plan view.

An image pickup device 11 and light emitting elements 12 are mounted on the first substrate 10. A front in-vivo image illuminated by the light emitting elements 12 is acquired by the image pickup device 11. The first substrate 10 includes a plurality of external electrodes 19 electrically connected to one of the image pickup device 11 and the light emitting elements 12. The second substrate 20 is a circuit substrate on which electronic components 21, such as CPUs, configured to control the image pickup unit 2 or the like are mounted. The second substrate 20 includes a plurality of connection electrodes 27, 28, and 29 electrically connected to the electronic components 21. The batteries 40 and 50 are button batteries configured to supply drive power.

The third substrate 30 includes connection electrodes 39 and is a transmission substrate on which an electronic component for wirelessly transmitting image data is mounted. The fourth substrate 60 is a power source substrate on which an electronic component for converting the power from the batteries 40 and 50 to drive signals is mounted, and the fourth substrate 60 includes connection electrodes 69. Note that the external electrodes 19 of the first substrate 10, the connection electrodes 27, 28, and 29 of the second substrate 20, and the connection electrodes 39 of the third substrate have substantially the same configuration. Note that other than the already described components, various electronic components, such as a chip capacitor, a diode, a chip resistance, and a chip inductor, may be mounted on each substrate.

The substrates of the image pickup unit 2 are not limited to the substrates described above. For example, in place of the first substrate 10, an illumination substrate on which light emitting elements are mounted and an image pickup substrate on which an image pickup device is mounted may be used. In this case, the image pickup substrate is assumed to be the first substrate. The number of batteries may be one, and a spacer for adjusting arrangement positions may be included.

The first substrate 10, the second substrate 20, the third substrate 30, the batteries 40 and 50, and the fourth substrate 60 are housed inside of the housing 5 in a state that respective main surfaces are arranged in parallel, and respective centers are arranged along the center axis O.

The first substrate 10 is electrically connected to a flexible first intermediate wiring board 70. Note that hereinafter, "electrically connected" will be simply stated as "connected".

The second substrate 20 is connected to a second intermediate wiring board 80, a third intermediate wiring board 35, and a fourth intermediate wiring board 45, all of which are flexible. The fourth substrate 60 is connected to a flexible fifth intermediate wiring board 55.

An outer diameter D40 of the batteries 40 and 50 is greater than outer diameters of the first substrate 10, the second substrate 20, the third substrate 30, and the fourth substrate 60. As described later, the first intermediate wiring board 70, the second intermediate wiring board 80, and the like are also arranged in a space at an extension position of a periphery of the battery 40 in a center axis direction. That is, the outer diameter D40 of the batteries 40 and 50 is a maximum outer diameter of the image pickup unit 2.

As shown in FIGS. 3A and 3B, the first substrate 10, the first intermediate wiring board 70, the second intermediate wiring board 80, the second substrate 20, and the fourth intermediate wiring board 45 are linked in a linearly arranged state. A conductor plate 45A serving as a point of contact with the battery 40 is further connected to the fourth intermediate wiring board 45. The third substrate 30 is connected to the second substrate 20 through the third intermediate wiring board 35 linked in a state that the third substrate 30 is arranged in a direction orthogonal to the second intermediate wiring board 80. A conductor plate 55A serving as a point of contact with the battery 50 is also connected to the fifth intermediate wiring board 55 connected to the fourth substrate 60.

Hereinafter, connection of the first intermediate wiring board 70 and the second intermediate wiring board 80 will be described in detail.

Figure 4:
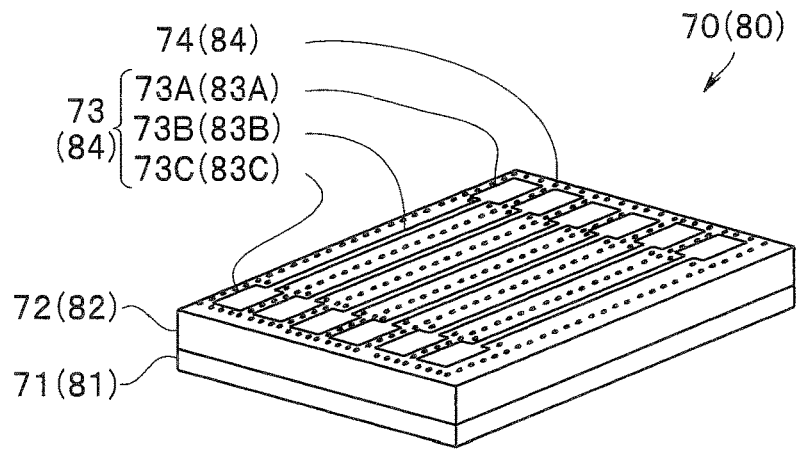
FIG. 4 is a perspective view of an intermediate wiring board of the image pickup unit of the first embodiment.

As shown in FIG. 4, the first intermediate wiring board 70 includes a flexible substrate 71, an adhesive layer 72 located on an entire surface of one surface of the substrate 71, and a plurality of wires 73 located on the adhesive layer 72. The wires 73 include first electrode pads 73A, wiring portions 73B, and third electrode pads 73C. Note that the second intermediate wiring board 80 has substantially the same configuration as the first intermediate wiring board 70 and includes a substrate 81, an adhesive layer 82, and second wires 83 including second electrode pads 83A, wiring portions 83B, and fourth electrode pads 83C. Sticky layer patterns 74 and 84 for temporary fixation are further located on the intermediate wiring boards 70 and 80.

Note that in the present specification, "adherence (adhere)" denotes a state of "fixation (fixing)" through a cured and solid adhesive layer. On the other hand, "sticking (stick)" denotes a state of "temporary fixation (temporary fixing)" through a soft sticky layer containing gel components. Peeling and reattachment are possible in the "temporary fixation". Furthermore, "close contact (closely contact)" denotes a state of surface contact.

Figure 5A:
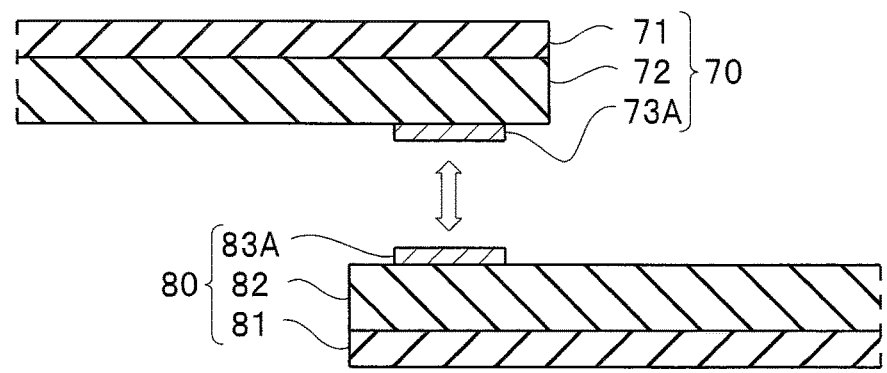
FIG. 5A is a cross-sectional view for describing a connection method of the image pickup unit of the first embodiment.
Figure 5B:
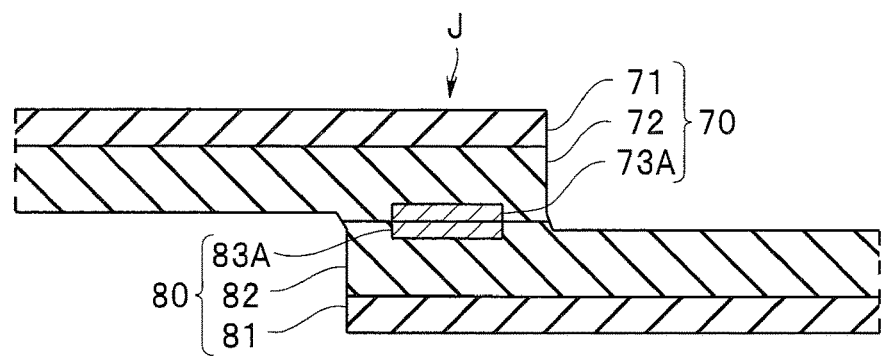
FIG. 5B is a cross-sectional view for describing the connection method of the image pickup unit of the first embodiment.

As shown in FIG. 5A, the first intermediate wiring board 70 and the second intermediate wiring board 80 are arranged such that the first electrode pads 73A and the second electrode pads 83A face each other. As shown in FIG. 5B, the first electrode pads 73A and the second electrode pads 83A are connected by pressing and bringing the pads into close contact. The first intermediate wiring board 70 and the second intermediate wiring board 80 are adhered by the adhesive layers 72 and 82 and fixed.

Next, to house the substrates inside of the housing 5, the linked first substrate 10, second substrate 20, and third substrate 30 are arranged such that main surfaces are parallel to each other. Miniaturization of the capsule endoscope 1 is strongly demanded to minimize invasion. To reduce the length, an interval D1 (see FIG. 2) between the first substrate 10 and the second substrate 20 is narrow and is, for example, 0.5 mm or more and 3 mm or less. On the other hand, an actual length D2 (see FIG. 3A) of the first intermediate wiring board 70 and the second intermediate wiring board 80 connecting the first substrate 10 and the second substrate 20 is set longer than D1 in consideration of variations in manufacturing.

However, the first electrode pads 73A and the second electrode pads 83A are flexible and are not bonded by using a non-flexible member such as soldering. Therefore, as shown in FIG. 2, a connection portion J of the first electrode pads 73A and the second electrode pads 83A can be bent and deformed into a concave state.

Preferably, D2 is 110% or more and 200% or less of D1. If D2 is equal to or greater than the range, the first substrate 10 and the second substrate 20 can be arranged parallel to each other at the predetermined interval D1. If D2 is equal to or smaller than the range, the connection portion J can be inserted between the first substrate 10 and the second substrate 20 by bending and deforming the connection portion J.

Note that parts of the third intermediate wiring board 35, the fourth intermediate wiring board 45, and the fifth intermediate wiring board 55 are also folded and are bent and deformed into a concave state. The batteries 40 and 50 are placed between the conductor plate 45A connected to the fourth intermediate wiring board 45 and the conductor plate 55A connected to the fifth intermediate wiring board 55.

The first intermediate wiring board 70 and the second intermediate wiring board 80 are bent and deformed and are arranged in the space at an extension position of peripheries of the batteries 40 and 50 in the center axis direction. The third intermediate wiring board 35, the fourth intermediate wiring board 45, and the fifth intermediate wiring board 55 are also arranged in the space at the extension position of the peripheries of the batteries 40 and 50 in the center axis direction. Therefore, the image pickup unit 2 has a small diameter.

Note that as described later, the first intermediate wiring board 70 and the second intermediate wiring board 80 are temporarily fixed through the sticky layer patterns 74 and 84 and are fixed through the adhesive layers 72 and 82 after action check is performed. Therefore, when there is an abnormality in one of the first substrate 10 and the second substrate 20, it is possible to replace only the substrate with the abnormality.

Therefore, the image pickup unit 2 and the endoscope 1 have small diameters, and productivity is high.

Note that the third intermediate wiring board 35, the fourth intermediate wiring board 45, and the fifth intermediate wiring board 55 may be formed by two intermediate wiring boards with a configuration similar to the first intermediate wiring board 70 and the second intermediate wiring board 80.

Figure 6:
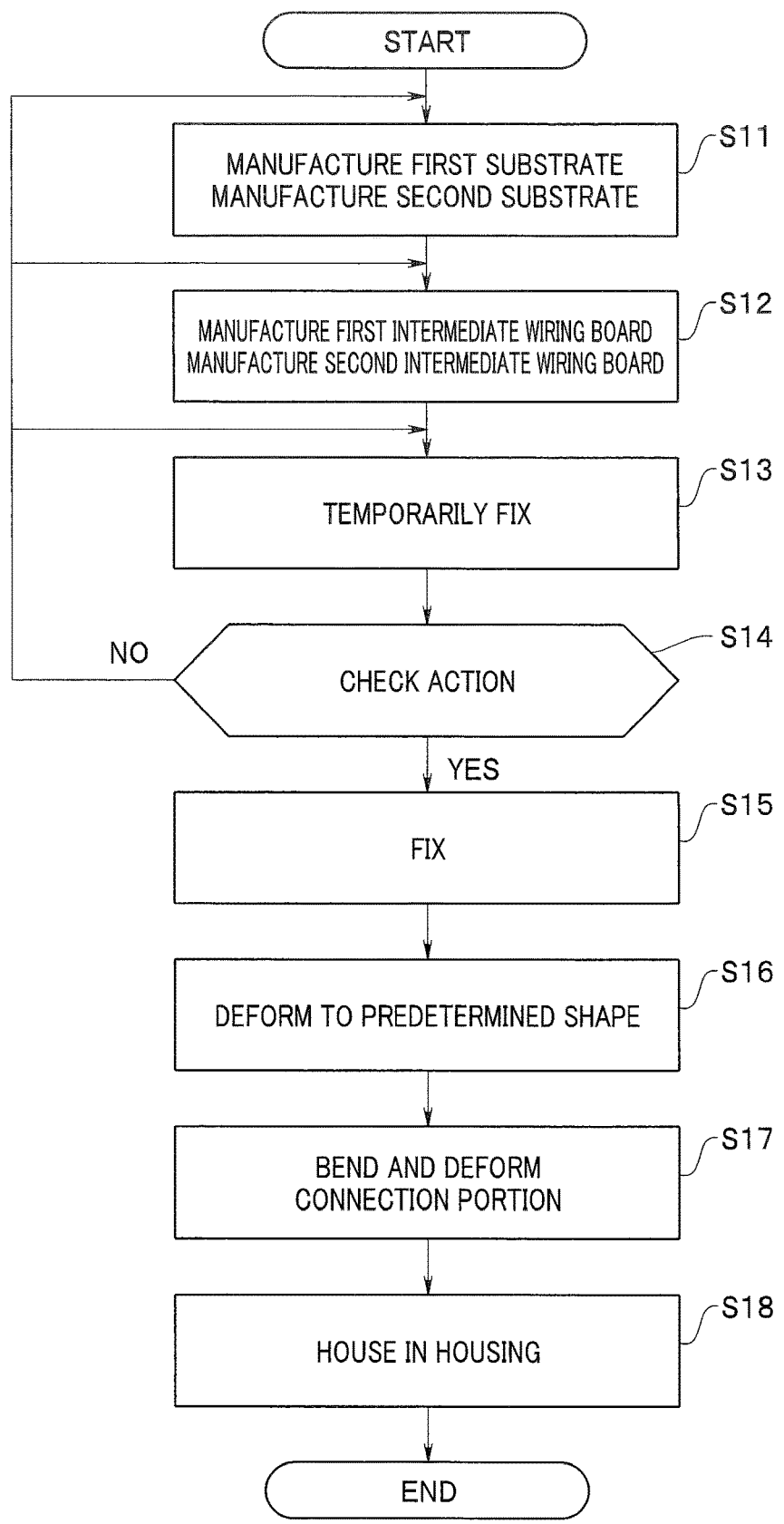
FIG. 6 is a flowchart of a manufacturing method of the capsule endoscope of the first embodiment.

Next, a manufacturing method of the capsule endoscope and the image pickup unit of the embodiment will be described along a flowchart of FIG. 6.

<Step S11> Manufacture First Substrate, Manufacture Second Substrate

The image pickup device 11, such as a CCD and a CMOS image sensor, and the light emitting elements 12, such as LEDs, are mounted on stud bumps or the like of the substantially circular, non-flexible first substrate 10 including, for example, a glass epoxy resin as a base material. As the image pickup device 11 and the light emitting elements 12 are mounted, the image pickup device 11 and the light emitting elements 12 are connected to the respective external electrodes 19.

The electronic components 21 are mounted on the substantially circular, non-flexible second substrate 20. As the electronic components 21 are mounted, the electronic components 21 are connected to the respective connection electrodes 29.

<Step S12> Manufacture First Intermediate Wiring Board, Manufacture Second Intermediate Wiring Board The first intermediate wiring board 70 is manufactured and connected to the first substrate 10, and the second intermediate wiring board 80 is manufactured and connected to the second substrate 20.

The third electrode pads 73C of the first intermediate wiring board 70 are connected to the external electrodes 19 of the first substrate 10. Note that in each substrate, a flexible substrate may be adhered to a non-flexible substrate. For example, in the first substrate 10, a polyimide substrate on which the image pickup device 11 and the like are mounted may be adhered to a non-flexible substrate. Furthermore, the external electrodes 19 and the third electrode pads 73C may be immediately fixed without the temporary fixation. As described later, ultraviolet radiation is used for the fixation.

Furthermore, the third intermediate wiring board 35 is connected and fixed to the connection electrodes 27 of the second substrate 20, and the fourth intermediate wiring board 45 is connected and fixed to the connection electrodes 28.

Note that the third substrate 30 and the fourth substrate 60 are also separately manufactured. The fifth intermediate wiring board 55 is connected and fixed to the connection electrodes 69 of the fourth substrate 60.

Note that although the connection in step S12 may be solder bonding, it is preferable that the connection is performed at a temperature equal to or lower than 250° C.

For example, it is preferable that one end of the first wire 73 of the first intermediate wiring board 70 includes the third electrode pad 73C, the external electrodes 19 of the first substrate 10 are fixed by the adhesive layer 72 in a state that the external electrodes 19 are in close contact with and electrically connected to the third electrode pads 73C, one end of the second wire 83 of the second intermediate wiring board 80 includes the fourth electrode pad 83C, and the connection electrodes 27 of the second substrate 20 are fixed by the adhesive layer 72 in a state that the connection electrodes 27 are in close contact with and electrically connected to the fourth electrode pads 83C.

<Step S13> Temporarily Fix

As shown in FIG. 5A, the first intermediate wiring board 70 and the second intermediate wiring board 80 are arranged such that the first electrode pads 73A and the second electrode pads 83A face each other. The first electrode pads 73A and the second electrode pads 83A are temporarily fixed through the sticky layer patterns 74 and 84 in a state that the first electrode pads 73A and the second electrode pads 83A are connected by being pressed and coming into close contact. Note that although the adhesive layers 72 and 82 also come into close contact when the first electrode pads 73A and the second electrode pads 83A are temporarily fixed, the adhesive layers 72 and 82 are not cured. Therefore, the effect of the adhesive layers 72 and 82 on the peel strength is significantly small and can be ignored.

Note that it is preferable that the thickness of the sticky layer pattern 74 of the first intermediate wiring board 70 is 10 μm or more and 500 μm or less. For example, the sticky layer pattern 74 is formed by a gel sticker, in which a gel fraction is 30% or more by weight and 70% or less by weight. For the gel fraction, the sticker is immersed in toluene and left for 24 hours. Remained insoluble matters are dried, and the mass is measured. The gel fraction is indicated by a percentage with respect to the original mass.

Figure 7A:
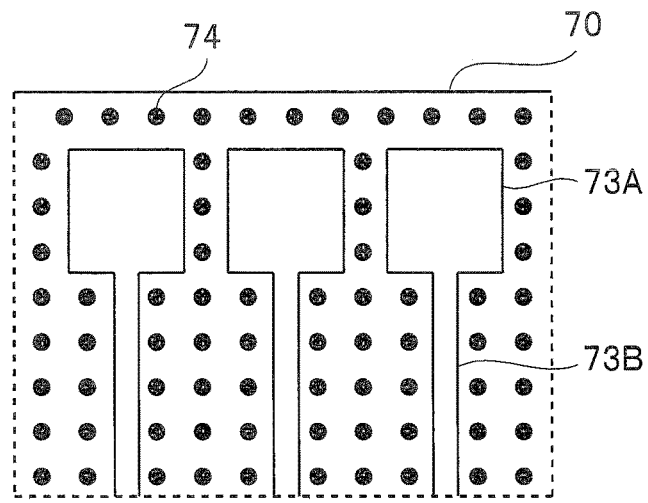
FIG. 7A is a top view of the intermediate wiring board of the image pickup unit of the first embodiment.

As shown in FIG. 7A, the sticky layer pattern 74 is provided as a dot pattern on the adhesive layer 72 around the wires 73. The first intermediate wiring board 70 can be temporarily fixed by the sticky layer pattern 74. That is, the peel strength (180 degree peel test, ISO 29862 2007) of the second intermediate wiring board 80 attached through the sticky layer patterns 74 and 84 is, for example, 0.05 N/10 mm or less. The second intermediate wiring board 80 can be easily peeled and can also be reattached. Note that, on the other hand, the peel strength of the adhesive layer 72 after the curing process is, for example, 0.5 N/10 mm or more.

Figure 7B:
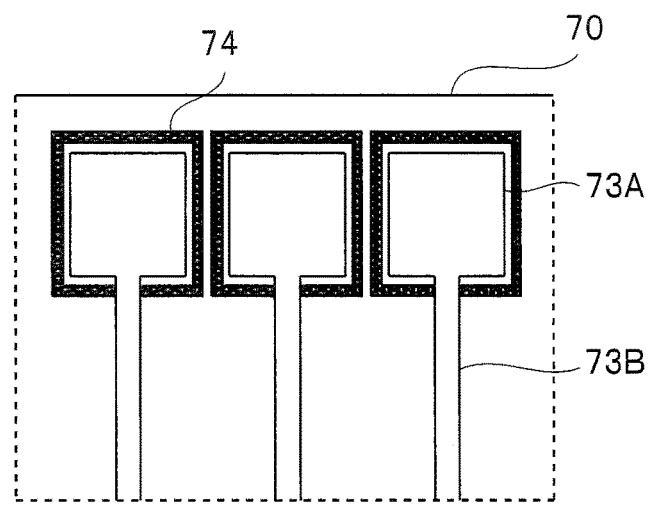
FIG. 7B is a top view of the intermediate wiring board of an image pickup unit according to a first modification of the first embodiment.
Figure 7C:
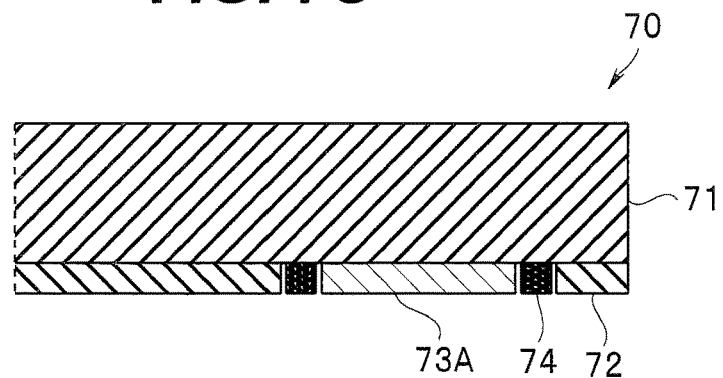
FIG. 7C is a cross-sectional view of an intermediate wiring board of an image pickup unit according to a second modification of the first embodiment.

On the other hand, the sticky layer pattern 74 of the intermediate wiring board 70 of a first modification shown in FIG. 7B is arranged in a frame shape only around the first electrode pads 73A. In the intermediate wiring board 70 of a second modification shown in FIG. 7C, each of the patterned adhesive layer 72, the sticky layer pattern 74 and the wires 73 is located on the substrate 71. That is, the adhesive layer 72 is not located on the entire surface of the intermediate wiring board 70. Furthermore, the sticky layer patter 74 is located on the substrate 71, not through the adhesive layer 72.

Although not shown, the adhesive layer may have a function of a sticky layer pattern with a small peel strength before the curing process in the intermediate wiring board. That is, the sticky layer pattern may function as an adhesive layer with a large peel strength based on the curing process. Furthermore, the substrate 71 of the intermediate wiring board may have a function of the adhesive layer 72.

Furthermore, the third intermediate wiring board 35 connected to the second substrate 20 is connected to the third substrate 30 and temporarily fixed. The conductor plate 45A is connected to the fourth intermediate wiring board 45. The conductor plate 55A is connected to the fifth intermediate wiring board 55 connected to the fourth substrate 60. Obviously, any of the connections may be temporary fixation through the sticky layer pattern.

<Step S14> Check Action

In the temporarily fixed state, the same DC voltage as the voltage of the batteries 40 and 50 is applied between the conductor plate 45A connected to the fourth intermediate wiring board 45 and the conductor plate 55A connected to the fifth intermediate wiring board 55. Consequently, the image pickup unit 2 enters a drive state and performs predetermined action. For example, the image pickup device 11 picks up an image according to light emitting timing of the light emitting elements 12, and image data is wirelessly transmitted.

If the image data is normally received by a reception apparatus arranged nearby (S14: YES), a process of step S15 is executed. If the image data cannot be received (S14: NO), one of the constituent elements and the connections has a problem. Therefore, the process returns to one of the steps of S11 to S13, and action checking inspection is performed again.

In the present manufacturing method, the first intermediate wiring board 70 and the second intermediate wiring board 80 are temporarily fixed and can be easily peeled. Furthermore, for example, the first substrate 10 connected with the first intermediate wiring board 70 can be replaced by another first substrate connected with a first intermediate wiring board. Therefore, the manufacturing method of the capsule endoscope 1 and the manufacturing method of the image pickup unit 2 do not cause much waste even if part of the members is defective. The manufacturing cost can be significantly reduced, and the productivity is high.

<Step S15> Fix (Cure)

A curing process of the adhesive layers 72 and 82 is executed, and the first intermediate wiring board 70 and the second intermediate wiring board 80 are fixed. The curing process is selected according to the material of the adhesive layer. For example, an active energy ray, such as an ultraviolet ray, transmitted through the substrate 71 is applied, and a heat treatment at 250° C. or lower is performed.

<Step S16> Deform to Predetermined Shape

The first substrate 10, the second substrate 20, the third substrate 30, and the conductor plate 45A are arranged such that the respective main surfaces are parallel, and the respective centers are along the center axis O. That is, the connection portion J of the connected first intermediate wiring board 70 and second intermediate wiring board 80, the third intermediate wiring board 35, and the fourth intermediate wiring board 45 are bent.

Separately, the main surface of the conductor plate 55A connected to the fourth substrate 60 and the main surface of the fourth substrate 60 are arranged to be parallel. That is, the fifth intermediate wiring board 55 is bent.

The batteries 40 and 50 are placed between the conductor plate 45A connected to the fourth intermediate wiring board 45 and the conductor plate 55A connected to the fifth intermediate wiring board 55.

<Step S17> Bend and Deform Connection Portion

Figure 8:
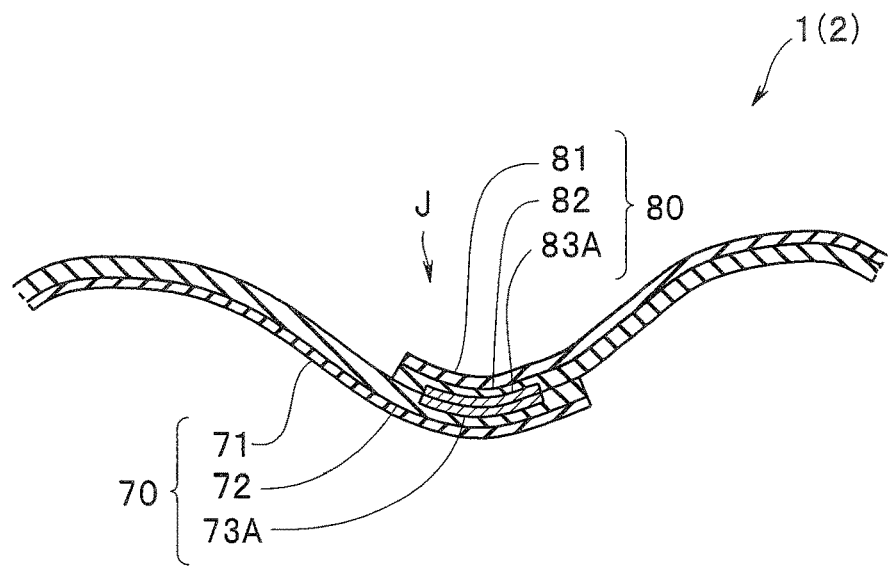
FIG. 8 is a cross-sectional view of a connection portion of the image pickup unit of the first embodiment.

As shown in FIG. 8, the connection portion J of the first intermediate wiring board 70 and the second intermediate wiring board 80, that is, the first electrode pads 73A and the second electrode pads 83A fixed in the closely contact state, is bent and deformed into a concave state and inserted between the first substrate 10 and the second substrate 20. Therefore, the first intermediate wiring board 70 and the second intermediate wiring board 80 are also arranged in the space at the extension position of the peripheries of the batteries 40 and 50 in the center axis direction.

<Step S18> House in Housing

The image pickup unit 2 is housed inside of the housing 5. That is, the inner diameter D5 of the housing 5 is slightly greater than the maximum outer diameter D40 of the image pickup unit 2. Therefore, the capsule endoscope 1 has a small diameter.

As described, the productivity of the manufacturing method of the capsule endoscope and the manufacturing method of the image pickup unit of the embodiment is high.

Note that although an example of the capsule endoscope 1 is described in the description above, similar advantageous effects are also attained in various capsule medical devices, such as a capsule medical device for extracting digestive fluid, a swallowing pH sensor, and a drug delivery system.

<Second Embodiment>

Next, an image pickup unit 2A of a second embodiment will be described. The image pickup unit 2A is similar to the image pickup unit 2. Therefore, the same reference signs are provided to the components with the same functions, and the description will not be repeated.

Figure 9:
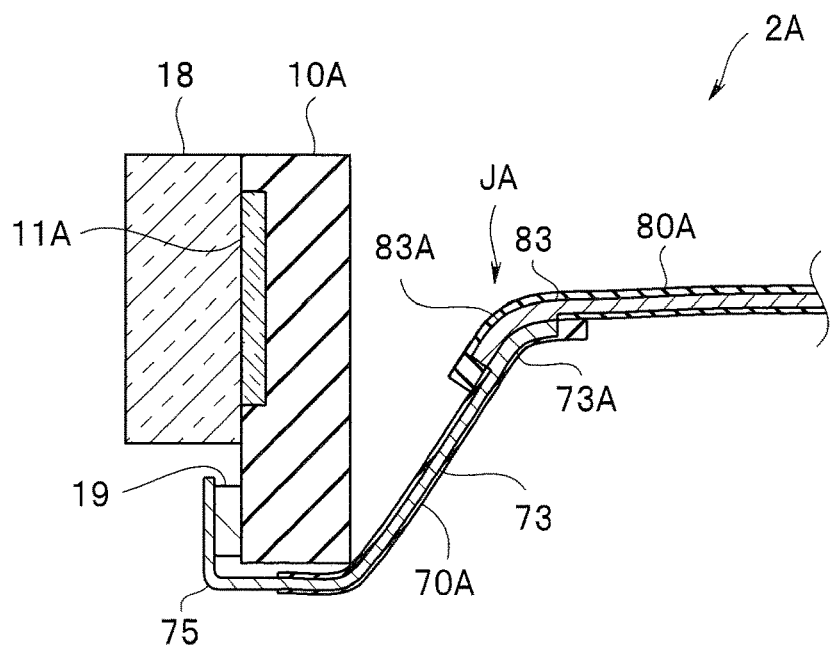
FIG. 9 is cross-sectional view of an image pickup unit of a second embodiment.

That is, as shown in FIG. 9, a configuration of a connection portion JA is similar to the configuration of the connection portion J of the image pickup unit 2. Note that the adhesive layer and the like are not displayed in FIG. 9.

As shown in FIG. 9, the image pickup unit 2A includes a glass lid 18, an image pickup device 10A equivalent to the first substrate, a flexible substrate 70A that is a first intermediate wiring board, and a flexible substrate 80A that is a second intermediate wiring board. The glass lid 18 is adhered to a light receiving section 11A formed on the image pickup device 10A through an adhesive resin. The glass lid 18 made of transparent glass protects the light receiving section 11A. The external electrodes 19 connected to the image pickup device 10A are bonding pads provided with stud bumps.

One end of the first wire 73 of the flexible substrate 70A forms an inner lead 75, and the other end includes the first electrode pad 73C. One end of the second wire 83 of the flexible substrate 80A includes the second electrode pad 83C.

The flexible substrate 70A and the flexible substrate 80A have the same configurations as those of the first intermediate wiring board 70 and the like. Therefore, the flexible substrate 70A can be fixed after the flexible substrate 70A is connected to the flexible substrate 80A and temporarily fixed.

In the manufacturing method of the image pickup unit 2A, the electrode pads of the flexible substrate can be connected and temporarily fixed after electronic components not shown are mounted on the flexible substrates 70A and 80A. Therefore, only a defective member needs to be replaced even if there is a malfunction in one of the members, and the cost can be significantly reduced.

Furthermore, in connecting the flexible substrates, a high temperature treatment is not performed, and a heavy load is not applied. Therefore, the damage of the components and the image pickup devices mounted on each substrate can be reduced.

Figure 10:
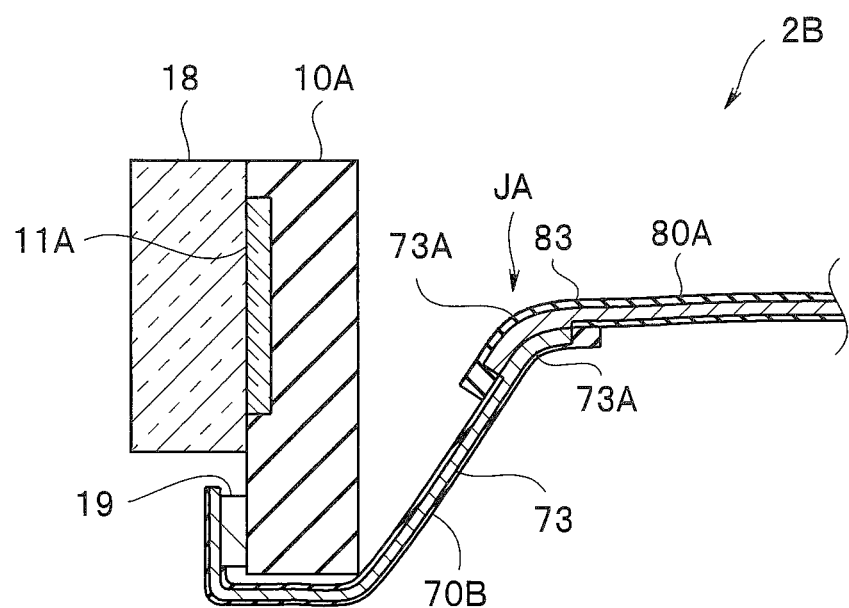
FIG. 10 is a cross-sectional view of an image pickup unit according to a modification of the second embodiment.

Note that in an image pickup unit 2B of a modification of the second embodiment shown in FIG. 10, a part exposed to the surface of the first wire 73 of the flexible substrate 70B is connected to the external electrode 19.

The image pickup unit 2B has the same advantageous effect as the image pickup unit 2A. That is, the first electrode pads 73A and the second electrode pads 83A fixed in the closely contact and electrically connected state are bent and deformed, and the diameter is small.

Having described the preferred embodiments of the invention referring to the accompanying drawings, it should be understood that the present invention is not limited to those precise embodiments and various changes an modifications thereof could be made by one skilled in the art without departing from the spirit or scope of the invention as defined in the appended claims.

What is claimed is:

1. An image pickup unit comprising:
a first substrate on which an image pickup device is mounted;
a first intermediate wiring board including a first wire, one end of the first wire electrically being connected to the first substrate, another end of the first wire including a first electrode pad;
a second substrate on which an electronic component is mounted; and
a second intermediate wiring board separately formed from the first intermediate wiring board, the second intermediate wiring board including a second wire, one end of the second wire being electrically connected to the second substrate, another end of the second wire including a second electrode pad, wherein
the first electrode pad and the second electrode pad being attached at a connection portion in an electrically connected state, the first and second electrode pads, while attached, are bent and deformed at the connection portion from a first configuration to a second configuration, the second configuration being bent and deformed relative to the first configuration; and
at least one of the first intermediate wiring board and the second intermediate wiring board includes a first adhesive and a second adhesive, the first adhesive being configured to allow easier removal of the attachment between the first and second electrode pads than the second adhesive.

2. The image pickup unit according to claim 1, wherein the image pickup unit is housed in a housing of a capsule endoscope.

3. A capsule endoscope comprising:
a first substrate on which an image pickup device is mounted, the first substrate including an external electrode electrically connected to the image pickup device;
a flexible first intermediate wiring board including a first wire, one end of the first wire being electrically connected to the external electrode, another end of the first wire including a first electrode pad;
a second substrate on which an electronic component is mounted, the second substrate including a connection electrode electrically connected to the electronic component;
a flexible second intermediate wiring board separately formed from the first intermediate wiring board, the second intermediate wiring board including a second wire, one end of the second wire being electrically connected to the connection electrode, another end of the second wire including a second electrode pad coming into close contact with the first electrode pad and fixed in an electrically connected state; and
a housing in which the first substrate, the second substrate, the first intermediate wiring board, and the second intermediate wiring board are housed, the housing being a capsule in a rotationally symmetric shape with a center axis in a longitudinal direction serving as an axis of rotational symmetry, wherein
a main surface of the first substrate and a main surface of the second substrate are arranged in parallel,
the first electrode pad and the second electrode pad being attached at a connection portion in an electrically connected state, the first and second electrode pads, while attached, are bent and deformed at the connection portion from a first configuration to a second configuration, the second configuration being bent and deformed relative to the first configuration, the first and second electrode pads, while attached are inserted between the first substrate and the second substrate; and
at least one of the first intermediate wiring board and the second intermediate wiring board includes a first adhesive and a second adhesive, the first adhesive being configured to allow easier removal of the attachment between the first and second electrode pads then the second adhesive.

4. The capsule endoscope according to claim 3, further comprising
a battery, a main surface of which is arranged parallel to the main surface of the first substrate, wherein
the first substrate, the second substrate, the first intermediate wiring board, and the second intermediate wiring board are arranged in a space at an extension position of a periphery of the battery in the center axis direction.

5. The capsule endoscope according to claim 4, wherein the one end of the first intermediate wiring board of the first wire of the first intermediate wiring board includes a third electrode pad,
the external electrode of the first substrate comes into close contact with the third electrode pad and is fixed in an electrically connected state by the second adhesive,
the one end of the second intermediate wiring board of the second wire of the second intermediate wiring board includes a fourth electrode pad, and
the connection electrode of the second substrate comes into close contact with the fourth electrode pad and is fixed in an electrically connected state by the second adhesive.

6. A manufacturing method of a capsule endoscope, in which an image pickup unit including a first substrate, a second substrate, a first intermediate wiring board, and a second intermediate wiring board is housed in a housing, and the first substrate and the second substrate are electrically connected through the first intermediate wiring board and the second intermediate wiring board, the manufacturing method comprising:
mounting an image pickup device on the first substrate including an external electrode to electrically connect the image pickup device and the external electrode;
mounting an electronic component on the second substrate including a connection electrode to electrically connect the electronic component and the connection electrode;
manufacturing the first intermediate wiring board including a first wire, one end of the first wire being electrically connected to the external electrode, another end of the first wire including a first electrode pad, and manufacturing the second intermediate wiring board including a second wire, one end of the second wire being electrically connected to the connection electrode, another end of the second wire including a second electrode pad;
temporarily fixing the first electrode pad and the second electrode pad by a sticky layer pattern around the first electrode pad, in a state that the first electrode pad and the second electrode pad are in close contact and electrically connected;
supplying drive power to the image pickup device through the second substrate to check action;
curing an adhesive layer around the first electrode pad to fix the first electrode pad and the second electrode pad;
arranging a main surface of the first substrate and a main surface of the second substrate parallel to each other;
bending and deforming the fixed first electrode pad and the second electrode pad to insert the fixed first electrode pad and the second electrode pad between the first substrate and the second substrate; and
housing the image pickup unit including the first substrate, the second substrate, the first intermediate wiring board, and the second intermediate wiring board in the housing.

* * * * *